(12) United States Patent
Vaillancourt

(10) Patent No.: US 6,413,958 B2
(45) Date of Patent: Jul. 2, 2002

(54) 4-HYDROXY-1,8-NAPHTHYRIDINE-3-CARBOXAMIDES AS ANTIVIRAL AGENTS

(75) Inventor: Valerie A. Vaillancourt, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 09/808,872

(22) Filed: Mar. 15, 2001

Related U.S. Application Data

(60) Provisional application No. 60/190,978, filed on Mar. 21, 2000.

(51) Int. Cl.[7] ............ A61K 31/435; C07D 471/04
(52) U.S. Cl. ............ 514/234.5; 514/300; 544/127; 546/123
(58) Field of Search ............ 546/123; 514/300, 514/234.5; 544/127

(56) References Cited

U.S. PATENT DOCUMENTS

| | | | |
|---|---|---|---|
| 4,559,157 A | 12/1985 | Smith et al. | 252/90 |
| 4,568,649 A | 2/1986 | Bertoglio-Matte | 436/534 |
| 4,608,392 A | 8/1986 | Jacquet | 514/844 |
| 4,820,508 A | 4/1989 | Wortzman | 424/59 |
| 4,826,837 A | 5/1989 | Doria et al. | 514/248 |
| 4,886,800 A | 12/1989 | Resch | 514/234.5 |
| 4,938,949 A | 7/1990 | Borch et al. | 424/10 |
| 4,959,363 A | 9/1990 | Wentland | 514/234.5 |
| 4,992,478 A | 2/1991 | Geria | 514/782 |
| 5,753,666 A | 5/1998 | Beasley et al. | 514/258 |
| 5,891,878 A | 4/1999 | Beasley et al. | 514/247 |

FOREIGN PATENT DOCUMENTS

| | | | |
|---|---|---|---|
| EP | 0 978 516 A1 | 2/2000 | C07D/471/04 |
| WO | WO97/04775 | 2/1997 | A61K/21/435 |
| WO | WO98/11073 | 3/1998 | C07D/215/48 |
| WO | WO99/07704 | 2/1999 | C07D/471/04 |
| WO | WO99/32450 | 7/1999 | C07D/215/56 |
| WO | WO99/38867 | 8/1999 | C07D/471/04 |

OTHER PUBLICATIONS

Cook, N.D., et al., *Pharmaceutical Manufacturing International*. pp. 49–53, 1992.
Takeuchi, Laboratory Practice, pp. 12 and 13, Sep., 1992.
Vaillancourt, Valerie, "Napthalene Carboxamides as Inhibitors of Human Cytomegalovirus DNA Polymerase," *Bioorganic and Medicinal Chemistry Letters*, Oxford, Great Britain, vol. 10, No. 18, pp. 2079–2081, Sep. 2000.
Wentland, et. al. "3–Quinolinecarboxamides. A series of Novel Orally–Active Antiherpetic Agents." *Journal of Medicinal Chemistry*. American Chemical Society. Washington, USA. vol. 36, No. 11, pp. 1580–1596.

*Primary Examiner*—Bernard Dentz
(74) *Attorney, Agent, or Firm*—Andrew M. Solomon; Lucy X. Yang

(57) ABSTRACT

Certain novel 4-hydroxy-1,8-naphthyridine-3-carboxamides. The compounds are effective in the treatment or prevention of viral infections, particularly viral infections caused by herpes simplex viruses types 1 and 2, human herpes viruses types 6, 7 and 8, varicello zoster viruses, human cytomegaloviruses and Epstein-Barr viruses.

20 Claims, No Drawings

4-HYDROXY-1,8-NAPHTHYRIDINE-3-CARBOXAMIDES AS ANTIVIRAL AGENTS

CROSS-REFERENCE TO RELATED APPLICATIONS

This application claims the benefit of the following provisional application: U.S. Ser. No. 60/190,978, filed Mar. 21, 2000.

BACKGROUND OF THE INVENTION

1. Field of the Invention

The present invention provides novel 1,8-naphthyridines, which are useful as antiviral agents (e.g. as agents against viruses of the herpes family).

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infections mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. No. 4,826,837 discloses 4-hydroxycinnoline-3-carboxamides and their use for the treatment of neoplastic diseases and acute and chronic infections of both bacterial and viral origin in mammals.

U.S. Pat. No. 4,886,800 discloses 4-substituted-cinnoline-3-carboxylic acids and 3-acyl-4-substituted-cinnoline derivatives and their use as central nervous system depressants.

U.S. Pat. Nos. 5,753,666 and 5,891,878 and WO 97/04775 disclose 1-alkyl-substituted-quinolone-3-carboxamides that are alleged to have therapeutic utility via inhibition of Phosphodiesterase IV esterase and/or Tumor Necrosis factor activity.

WO 99/38867 discloses 1-cycloalkyl-1,8-naphthyridin-4-one derivatives; pharmacologically acceptable salts or solvates thereof; and a phosphodiesterase IV inhibitor containing any of the above as an active ingredient.

WO 99/07704 discloses N-1-aryl and heteroaryl 1,8 naphthyridines as phosphodiesterase IV inhibitors.

Commonly assigned PCT/US98/25192 discloses 4-hydroxyquinoline-3-carboxamides and hydrazides as antiviral agents.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are 4-hydroxy[1,8] naphthyridine-3-carboxamides which are useful as antiviral agents, particularly against herpes viruses.

Even more specifically, the compounds are of formula (IV)

A compound of formula IV:

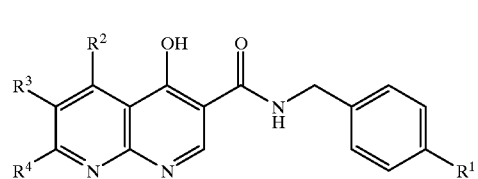

IV or a pharmaceutically acceptable salt thereof wherein, $R^1$ is
(a) Cl,
(b) Br,
(c) CN,
(d) $NO_2$, or
(e) F;

$R^2$, $R^3$ and $R^4$ are independently selected from:
(a) H,
(b) halo,
(c) aryl,
(d) $S(O)_m R^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7 R^8$,
(l) $SR^{10}$,
(m) Shet,
(n) $NHCOR^{12}$,
(o) $NHSO_2 R^{12}$, or
(p) $C_{1-7}$alkyl which may be partially unsaturated and optionally substituted by one or more substituents of the group $R^{11}$, $OR^{13}$, $SR^{10}$, $SR^{13}$, $NR^7 R^8$, halo, $(C=O)C_{1-7}$alkyl, or $SO_m R^9$;

$R^6$ is
(a) $C_{1-7}$alkyl,
(b) $NR^7 R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_m R^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
- (a) H,
- (b) methyl, or
- (b) $C_{2-7}$alkyl optionally substituted by OH;

$R^{11}$ is
- (a) $OR^{10}$,
- (b) Ohet,
- (c) Oaryl,
- (d) $CO_2R^{10}$,
- (e) het,
- (f) aryl, or
- (g) CN;

$R^{12}$ is
- (a) H,
- (b) het,
- (c) aryl,
- (d) $C_{3-8}$cycloalkyl,
- (e) methyl, or
- (f) $C_{2-7}$alkyl optionally substituted by $NR^7R^8$ or $R^{11}$;

$R^{13}$ is
- (a) $(P=O)(OR^{14})_2$,
- (b) $CO(CH_2)_nCON(CH_3)-(CH_2)_nSO_3^-M^+$,
- (c) an amino acid,
- (d) C(=O)aryl, or
- (e) $C(=O)C_{1-7}$alkyl optionally substituted by $NR^7R^8$, aryl, het, $CO_2H$, or $O(CH_2)_nCO_2R^{14}$;

$R^{14}$ is
- (a) H, or
- (b) $C_{1-7}$alkyl;

each n is independently 1, 2, 3, 4 or 5;

each m is independently 0, 1, or 2;

M is sodium, potassium, or lithium;

aryl is a phenyl radical or an ortho-fused bicyclic carbocyclic radical wherein at least one ring is aromatic;

wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;

wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups.

In particularly preferred embodiments, $R^3$ is either $CH_2$-morpholine, $CH_2$-(tetrahydro-2H-pyran-4-yl), alkynl-$CH_2OH$ or $(CH_2)_3OH$.

Another embodiment of the present invention provides a pharmaceutical composition comprising a compound of formula (IV) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (IV) or a pharmaceutically acceptable salt thereof.

A further embodiment of the present invention comprises the use of a compound of formula (IV) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (IV) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical wherein at least one ring is aromatic. Het is a four- (4), five- (5), six- (6), or seven- (7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

To the extent that any pharmaceutically active compound is disclosed or claimed, it is expressly intended to include all active metabolites produced in vivo.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (I) or (II) having any combination of the values, specific values, more specific values, and preferred values described herein.

2. The Invention

The present invention provides compounds of formula (IV):

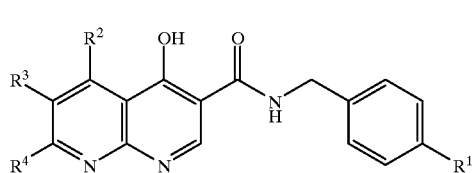

IV or a pharmaceutically acceptable salt thereof wherein, $R^1$ is
(a) Cl,
(b) Br,
(c) CN,
(d) $NO_2$, or
(e) F;

$R^2$, $R^3$ and $R^4$ are independently selected from:
(a) H,
(b) halo,
(c) aryl,
(d) $S(O)_m R^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7 R^8$
(l) $SR^{10}$,
(m) Shet,
(n) $NHCOR^{12}$,
(o) $NHSO_2 R^{12}$, or
(p) $C_{1-7}$alkyl which may be partially unsaturated and optionally substituted by one or more substituents of the group $R^{11}$, $OR^{13}$, $SR^{10}$, $SR^{13}$, $NR^7 R^8$, halo, $(C=O)C_{1-7}$alkyl, or $SO_m R^9$;

$R^6$ is
(a) $C_{1-7}$alkyl,
(b) $NR^7 R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_m R^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
(a) H,
(b) methyl, or
(b) $C_{2-7}$alkyl optionally substituted by OH;

$R^{11}$ is
(a) $OR^{10}$,
(b) Ohet,
(c) Oaryl,
(d) $CO_2 R^{10}$,
(e) het,
(f) aryl, or
(g) CN;

$R^{12}$ is
(a) H,
(b) het,
(c) aryl,
(d) $C_{3-8}$cycloalkyl,
(e) methyl, or
(f) $C_{2-7}$alkyl optionally substituted by $NR^7 R^8$ or $R^{11}$;

$R^{13}$ is
(a) $(P=O)(OR^{14})_2$,
(b) $CO(CH_2)_n CON(CH_3)-(CH_2)_n SO_3^- M^+$,
(c) an amino acid,
(d) $C(=O)$aryl, or
(e) $C(=O)C_{1-7}$alkyl optionally substituted by $NR^7 R^8$, aryl, het, $CO_2 H$, or $O(CH_2)_n CO_2 R^{14}$;

$R^{14}$ is
(a) H, or
(b) $C_{1-7}$alkyl;

each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, $CO_2 R^{14}$, $CF_3$, $C_{1-6}$alkoxy, and $C_{1-6}$alkyl which may be further substituted by one to three $SR^{14}$, $NR^{14}R^{14}$, $OR^{14}$, or $CO_2 R^{14}$ groups;
het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;

wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$alkyl which may be further substituted by one to three $SR^{14}$, $NR^{14}R^{14}$, $OR^{14}$, or $CO_2R^{14}$ groups.

Specifically, $C_{1-7}$alkyl can be methyl, ethyl, propyl, isopropyl, butyl, iso-butyl, sec-butyl, pentyl, 3-pentyl, hexyl, or heptyl; $C_{3-7}$cycloalkyl can be cyclopropyl, cyclobutyl, cyclopentyl, cyclohexyl, or cycloheptyl.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Particularly preferred compounds are those where $R^1$ is Cl and $R^3$ is either $CH_2$-morpholine, $CH_2$-(tetrahydro-2H-pyran-4-yl), alkynl-$CH_2OH$ or $(CH_2)_3OH$.

Specifically preferred compounds include, but are not limited to the following:

N-(4-chlorobenzyl)-4-hydroxy-7-methyl[1,8]naphthyridine-3-carboxamide;

N-(4-chlorobenzyl)-4-hydroxy-7-methyl-6-(tetrahydro-2H-pyran-4-ylmethyl)[1,8]naphthyridine-3-carboxamide;

6-bromo-N-(4-chlorobenzyl)-4-hydroxy-7-methyl[1,8]naphthyridine-3-carboxamide;

N-(4-chlorobenzyl)-4-hydroxy-6-(3-hydroxy-1-propynyl)-7-methyl[1,8]naphthyridine-3-carboxamide;

N-(4-chlorobenzyl)-4-hydroxy-6-iodo-7-methyl[1,8]naphthyridine-3-carboxamide;

N-(4-chlorobenzyl)-4-hydroxy-7-methyl-6-(4-morpholinylmethyl)[1,8]naphthyridine-3-carboxamide; and Methyl 6-{[(4-chlorobenzyl)amino]carbonyl}-5-hydroxy-2-methyl[1,8]naphthyridine-3-carboxylate.

The following Charts 1–3 describe the preparation of the compounds of the present invention. All of the starting materials and final compounds are prepared by procedures described in these charts or by procedures analogous thereto, which would be well known to one of ordinary skill in organic chemistry. All of the variables used in the charts are as defined below or as in the claims.

The basic ring system can be prepared according to Chart 1. Condensation of a substituted 2-aminopyridine with diethyl ethoxymethylenemalonate and subsequent cyclization provides the 1,8-naphthyridine-3-carboxylic ester. Treatment of this compound with 4-chlorobenzylamine provides the 1,8-naphthyridine-3-carboxamide.

Chart 1

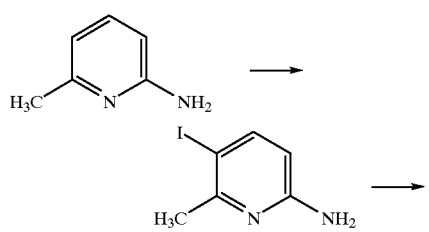

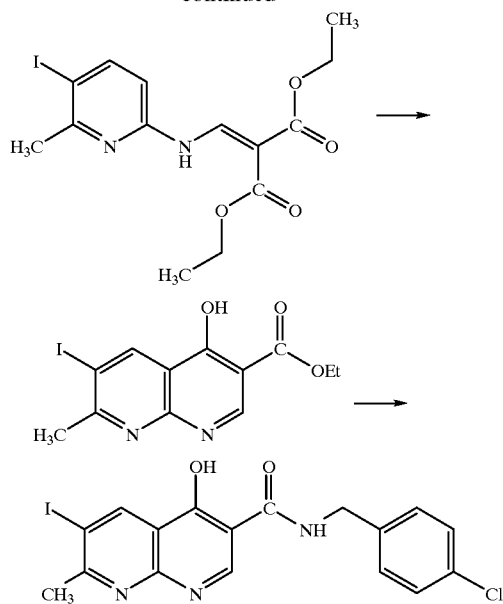

These ring systems can be further elaborated. One example of such an elaboration is shown in Chart 2. Palladium catalyzed coupling of the aryl iodide with an acetylene such as propargyl alcohol and subsequent reduction of the alkyne by hydrogenation provides the 6-(3-hydroxypropyl)-1,8-naphthyridine-3-carboxamide.

Chart 2

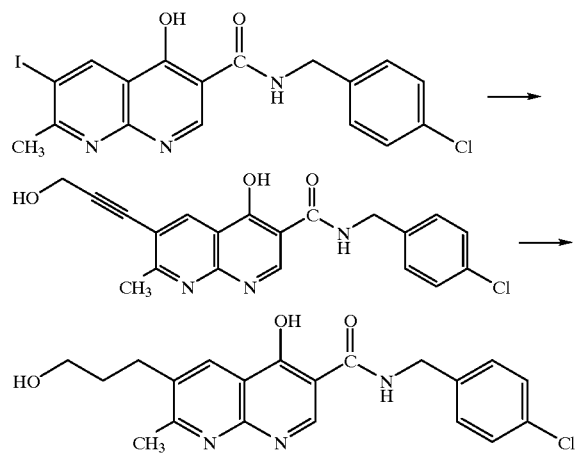

A second example of an elaboration is depicted in Chart 3. Palladium catalyzed carbomethylation of the aryl iodide provides the 7-methyl ester.

Chart 3

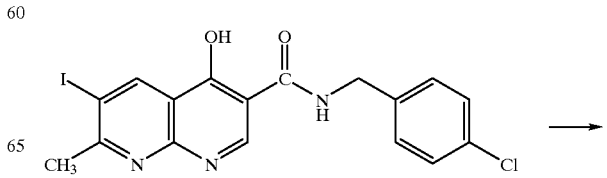

-continued

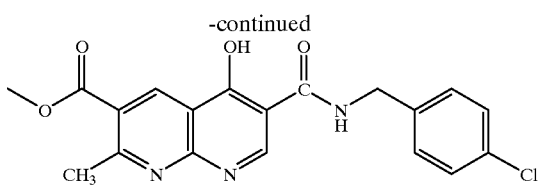

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). To the extent necessary for completion, this publication is expressly incorporated by reference. The compounds and compositions of the present invention can be administered parenterally (for example, by intravenous, intraperitoneal or intramuscular injection), topically, intranasally, orally, intravaginally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices including those relying on osmotic delivery such as the OROS type devices developed by the ALZA Corp.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, cyclodextrins and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula IV to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula IV can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock (e.g., food animals such as cows, pigs, goats, sheep, deer, etc.) and companion animals (e.g., dogs, cats, fish, horses and birds) is also specifically contemplated as falling within the scope of the instant invention.

The invention will be further described by the following non-limiting examples.

EXAMPLE 1

N-(4-chlorobenzyl)-4-hydroxy-7-methyl[1,8] naphthyridine-3-carboxamide

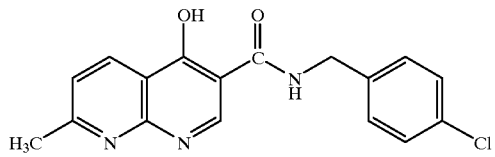

A solution of 4-hydroxy-7-methyl[1,8]naphthyridine-3-carboxylic acid (0.204 g) and 4-chlorobenzylamine (0.12 mL) is heated to reflux. To this is added dropwise phosphorus trichloride (0.04 mL). Refluxing is continued for 3 h. The mixture is cooled and water is added to destroy excess $PCl_3$. The solvents are removed. The residue is partitioned between EtOAc and water. The aqueous layer is extracted with EtOAc (3×). The combined organic layers are washed with brine (1×), dried and condensed. The residue is adsorbed on silica and chromatographed (eluent 5% MeOH/$CH_2Cl_2$). Fractions homogeneous by TLC are condensed and triturated with $Et_2O$/hexanes to yield 0.017 g (5%) of the desired product as a yellow solid. Physical characteristics are as follows: m.p. 280–285° C. (dec); $^1$H NMR (300 MHz, DMSO) δ 13.0, 10.20, 8.63, 8.47, 7.38, 4.52, 2.61; IR (mull) 3186, 3148, 3055, 3034, 1655, 1605, 1570, 1546, 1494, 1333, 1243, 1097, 814, 799, 623 $cm^{-1}$; MS (EI) m/z 327 ($M^+$), 188, 187, 161, 160, 142, 140, 132, 131, 104; HRMS (EI) calcd for $C_{17}H_{14}ClN_3O_2$ 327.0775, found 327.0783.

PREPARATION 1

Ethyl 6-bromo-4-hydroxy-7-methyl[1,8] naphthyridine-3-carboxylate

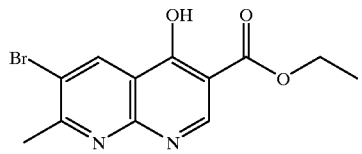

A solution of 6-amino-3-bromo-2-methylpyridine (1.89 g) and diethoxymethylenemalonate (2.16 g) is heated at 110° C. for 30 min. The reaction is cooled and the residue is recrystallized from EtOH. To the resulting solid is dissolved in 45 mL of $Ph_2O$. The mixture is heated to 250° C. for 3 h. The solution is then cooled to room temperature and the resulting precipitate is collected and dried. The crude product is chromatographed on silica (Biotage flash 40M, 2% MeOH/$CH_2Cl_2$ eluent). Fractions homogeneous by TLC are collected and concentrated to yield 1.075 g (35%) of the desired product as a yellow solid. Physical characteristics are as follows: m.p. 270° C. (dec.); $^1$H NMR (DMSO-$d_6$) δ 12.73, 8.49, 8.47, 4.21, 2.67, 1.27.

EXAMPLE 2

6-bromo-N-(4-chlorobenzyl)-4-hydroxy-7-methyl[1,8]naphthyridine-3-carboxamide

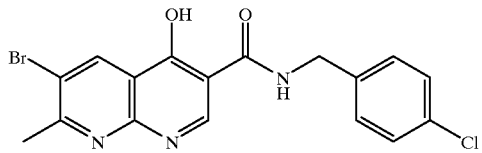

A solution of ethyl 6-bromo-4-hydroxy-7-methyl[1,8]naphthyridine-3-carboxylate (Prep 1 0.57 g) and 4-chlorobenzylamine (2.59 g) is heated to 180° C. for 1 h. The mixture is cooled and diluted with EtOAc. The resulting precipitate is collected and dried. Physical characteristics are as follows: m.p. 269–270° C.; $^1$H NMR (DMSO-$d_6$) δ 13.21, 10.09, 8.67, 8.62, 7.38, 4.54, 2.71; IR (drift) 3028, 2974, 2907, 1653, 1598, 1555, 1526, 1493, 1410, 1354, 1326, 1242, 1096, 806, 639 cm$^{-1}$; Anal. Calcd for $C_{17}H_{13}BrClN_3O_2$: C, 50.21; H, 3.22; N, 10.33; Found: C, 50.31; H, 3.23; N, 10.17.

EXAMPLE 3

N-(4-chlorobenzyl)-4-hydroxy-6-(3-hydroxy-1-propynyl)-7-methyl[1,8]naphthyridine-3-carboxamide

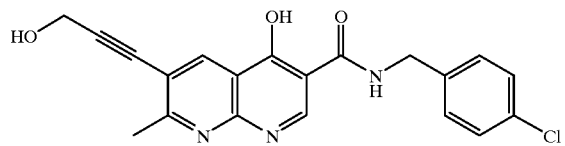

A solution of 6-bromo-N-(4-chlorobenzyl)-4-hydroxy-7-methyl[1,8]naphthyridine-3-carboxamide (Ex 2. 0.244 g), propargyl alcohol (0.047 g), triethylamine (0.38 mL) and PdCl$_2$(PPh$_3$)$_2$ (0.023 g) in 3 mL DMF is heated to 90° C. for 2.5 h. The resulting solution is cooled and partitioned between EtOAc and water. The solid which formed is filtered and discarded. The aqueous layer is extracted with EtOAc (3×). The combined organic layers are washed with brine, dried and condensed. The crude product is chromatographed on silica (Biotage flash 40S, eluent 2% MeOH/CH$_2$Cl$_2$ then 3% MeOH/CH$_2$Cl$_2$. Fractions homogeneous by TLC are combined and condensed to yield 0.081 g (35%) of the desired product as a yellow solid. Physical characteristics are as follows: m.p. 279–281° C. (dec.); $^1$H NMR (DMSO-$d_6$) δ 13.19, 10.12, 8.64, 8.43, 7.38, 5.46, 4.54, 4.40, 2.71; IR (drift) 3194, 3065, 2944, 1645, 1597, 1566, 1522, 1488, 1418, 1357, 1257, 1208, 1015, 851, 809 cm$^{-1}$; OAMS supporting ions at: ESI+381.9 ESI–379.9; HRMS (FAB) calcd for $C_{20}H_{16}ClN_3O_3$ +H$_1$ 382.0958, found 382.0960.

PREPARATION 2

2-amino-5-iodo-6-picoline

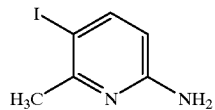

A mixture of 2-amino-6-picoline (5.40 g), periodic acid (2.28 g), and iodine (5.00 g) is heated in a solution of acetic acid (30 mL), water (6 mL), and sulfuric acid (0.9 mL) at 80° C. for 3 h. The reaction is cooled to room temperature and poured into 100 mL 10% aqueous sodium bisulfite. The aqueous solution is extracted with diethyl ether (3×100 mL). The combined organics are washed with 10% NaOH, then dried over Na$_2$SO$_4$, filtered, and concentrated. Purification by chromatography (eluent EtOAc) affords a yellow liquid. The liquid is further dried on the vacuum pump where it crystallizes to afford 2-amino-5-iodo-6-picoline (4.48 g, 38%). Physical characteristics are as follows: $^1$H NMR (300 MHz, DMSO-$d_6$) δ 7.60, 6.09, 6.05, 2.38.

PREPARATION 3

Diethyl 2-{[(5-iodo-6-methyl-2-pyridinyl)amino]methylene}malonate

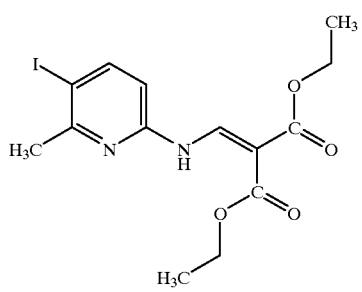

A solution of 2-amino-5-iodo-6-picoline (Prep 2 4.48 g) and diethyl ethoxymethylenemalonate (4.25 mL) is heated at 95° C. for 1.5 h. The reaction is cooled to room temperature. Hexanes (20 mL) are added and the resulting solid is filtered, washed with a minimal amount of hexanes, and dried to give the desired enamine (6.45 g, 83%). Physical Characteristics are as follows: m.p. 138–139° C.; $^1$H NMR (300 MHz, DMSO-$d_6$) δ 10.70, 8.96, 8.11, 7.03, 4.21, 4.14, 1.26, 1.24; IR (drift) 2989, 1686, 1641, 1603, 1568, 1548, 1421, 1373, 1363, 1333, 1272, 1251, 1232, 1211, 800 cm$^{-1}$; MS (ESI) m/z 404.9 (M+H)$^+$, 402.9 (M–H)$^-$; Anal. Calcd for $C_{14}H_{17}IN_2O_4$: C, 41.60; H, 4.24; N, 6.93; Found: C, 41.68; H, 4.35; N, 6.83.

PREPARATION 4

Ethyl 4-hydroxy-6-iodo-7-methyl[1,8]naphthyridine-3-carboxylate

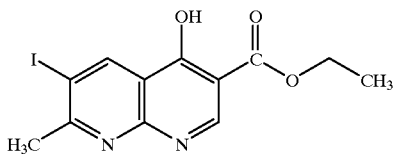

A solution of diethyl 2-{[(5-iodo-6-methyl-2-pyridinyl)amino]methylene}malonate Prep 3(1.09 g) in 20 mL diphenyl ether is heated at 250° C. for 2 h with removal of ethanol via a Dean-Stark trap. The reaction is cooled to room temperature. Hexanes (15 mL) are added and the solid is filtered, washed thoroughly with hexanes, and dried. The crude solid is dissolved in $CH_2Cl_2$/MeOH and adsorbed onto silica. Purification by chromatography (eluent $CH_2Cl_2$ (1L), 1% MeOH/$CH_2Cl_2$ (1L), 2% MeOH/$CH_2Cl_2$ (2L)) affords the product as a yellow-green solid (0.50 g, 52%). Physical characteristics are as follows: m.p. 275–277° C. (dec.); $^1$H NMR (300 MHz, DMSO-$d_6$) δ 12.80, 8.72, 8.47, 4.21, 2.74, 1.27; IR (drift) 2981, 1718, 1606, 1524, 1407, 1376, 1356, 1319, 1291, 1244, 1192, 1185, 1109, 809, 623 cm$^{-1}$; MS (ESI) m/z 358.9 (M+H)$^+$, 356.9 (M–H)$^-$; Anal. Calcd for $C_{12}H_{11}IN_2O_3$: C, 40.24; H, 3.10; N, 7.82; Found: C, 40.15; H, 3.05; N, 7.81.

EXAMPLE 4

N-(4-chlorobenzyl)-4-hydroxy-6-iodo-7-methyl[1,8]naphthyridine-3-carboxamide

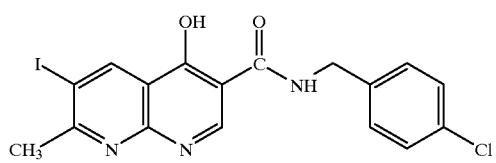

A solution of ethyl 4-hydroxy-6-iodo-7-methyl[1,8]naphthyridine-3-carboxylate Prep 4(0.41 g) and 4-chlorobenzylamine (2.50 mL) is heated at 180° C. for 1 h. The reaction is cooled to room temperature. Ethyl acetate (10 mL) and then hexanes (20 mL) are added and the solid is filtered, washed thoroughly with hexanes, and dried. The crude solid is dissolved in $CH_2Cl_2$/MeOH and adsorbed onto silica. Purification by chromatography (eluent $CH_2Cl_2$ (1L), 1% MeOH/$CH_2Cl_2$ (3L), 1.5% MeOH/$CH_2Cl_2$ (1L), 2% MeOH/$CH_2Cl_2$ (2L)) affords the desired product as a white solid (0.30 g, 0.66 mmol, 58%). Physical characteristics are as follows: m.p. 276–277° C.; $^1$H NMR (300 MHz, DMSO-$d_6$) δ 13.17, 10.10, 8.83, 8.66, 7.40, 7.35, 4.54, 2.77; IR (drift) 3063, 3022, 2957, 2895, 1650, 1596, 1552, 1521, 1493, 1405, 1352, 1323, 1241, 1095, 807 cm$^{-1}$; MS (ESI) m/z 453.6 (M+H)$^+$, 451.7 (M–H)$^-$; Anal. Calcd for $C_{17}H_{13}ClIN_3O_2$: C, 45.01; H, 2.89; N, 9.26; Found: C, 44.92; H, 2.78; N, 9.17.

EXAMPLE 5

Methyl 6-{[(4-chlorobenzyl)amino]carbonyl}-5-hydroxy-2-methyl[1,8]naphthyridine-3-carboxylate

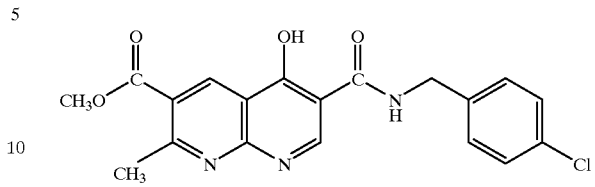

A flame-dried flask containing 5 mL anhydrous DMF is degassed with nitrogen for 15 minutes. To this is added N-(4-chlorobenzyl)-4-hydroxy-6-iodo-7-methyl[1,8]naphthyridine-3-carboxamide Ex-4(0.26 g), NEt$_3$ (0.16 mL), methanol (0.92 mL), and Pd(PPh$_3$)$_2$Cl$_2$ (0.043 g, 0.061 mmol). The reaction is placed under a CO balloon atmosphere and heated at 70° C. for 24 h. The reaction is cooled to room temperature and poured into 40 mL 1N HCl. The resulting solid is filtered and dried, then dissolved in $CH_2Cl_2$/MeOH and adsorbed onto silica. Purification by chromatography (eluent $CH_2Cl_2$ (1L), 1% MeOH/$CH_2Cl_2$ (1L), 1.5% MeOH/$CH_2Cl_2$ (1L), 2% MeOH/$CH_2Cl_2$ (1L), 2.5% MeOH/$CH_2Cl_2$ (1L)) affords the desired product as a beige solid (0.13 g, 59%). Physical characteristics are as follows: m.p. 265–267° C.; $^1$H NMR (300 MHz, DMSO-$d_6$) δ 13.28, 10.06, 8.96, 8.69, 7.41, 7.36, 4.55, 3.91, 2.85; IR (drift) 1729, 1657, 1602, 1556, 1525, 1494, 1438, 1421, 1358, 1267, 1236, 1195, 1134, 810, 784 cm$^{-1}$; MS (ESI) m/z 386.0 (M+H)$^+$, 384.1 (M–H)$^-$; HRMS (FAB) calcd for $C_{19}H_{16}ClN_3O_4$+Na 408.0727, found 408.0717.

Testing of Inventive Compounds

The antiviral activity of a compound of the invention can be determined using pharmacological models which are well known to the art, or using Test A described below.

The compounds of formula (IV) and pharmaceutically acceptable salts thereof are useful as antiviral agents. Thus, they are useful to combat viral infections in animals, including man. The compounds are generally active against herpes viruses, and are particularly useful against the varicella zoster virus (ZVZ), the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-cholamidopropyl)-dimethylammonio]-1- propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 μl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula IV in this assay are shown in Table 1. All results are listed as Polymerase $IC_{50}$ (μM) values. In Table 1, the term "nd" refers to activity data not determined.

| Example | HCMV |
|---------|------|
| 1 | 26 |
| 2 | 39% inhibition at 20 μm |
| 3 | 2.1 |
| 4 | 13.7 |
| 5 | 8.5 |

Having described the invention in detail and by reference to the preferred embodiments thereof, it will be apparent that modifications and variations are possible without departing from the scope of the appended claims.

What is claimed is:

1. A compound of formula IV:

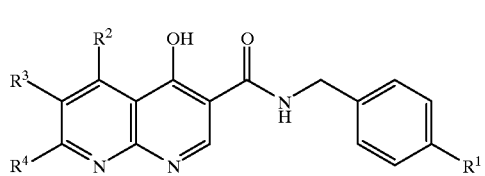

IV or a pharmaceutically acceptable salt thereof wherein, $R^1$ is
(a) Cl,
(b) Br,
(c) CN,
(d) $NO_2$, or
(e) F;

$R^2$, $R^3$ and $R^4$ are independently selected from:
(a) H,
(b) halo,
(c) aryl,
(d) $S(O)_m R^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7 R^8$,
(l) $SR^{10}$,
(m) Shet,
(n) $NHCOR^{12}$,
(o) $NHSO_2 R^{12}$, or
(p) $C_{1-7}$alkyl which may be partially unsaturated and optionally substituted by one or more substituents of the group $R^{11}$, $OR^{13}$, $SR^{10}$, $SR^{13}$, $NR^7 R^8$, halo, $(C=O)C_{1-7}$alkyl, or $SO_m R^9$;

$R^6$ is
(a) $C_{1-7}$alkyl,
(b) $NR^7 R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_m R^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
(a) H,
(b) methyl, or
(b) $C_{2-7}$alkyl optionally substituted by OH;

$R^{11}$ is
(a) $OR^{10}$,
(b) Ohet,
(c) Oaryl,
(d) $CO_2 R^{10}$,
(e) het,
(f) aryl, or
(g) CN;

$R^{12}$ is
(a) H,
(b) het,
(c) aryl,
(d) $C_{3-8}$cycloalkyl,
(e) methyl, or
(f) $C_{2-7}$alkyl optionally substituted by $NR^7 R^8$ or $R^{11}$;

$R^{13}$ is
- (a) $(P=O)(OR^{14})_2$,
- (b) $CO(CH_2)_nCON(CH_3)\text{-}(CH_2)_nSO_3^-M^+$,
- (c) an amino acid,
- (d) $C(=O)$aryl, or
- (e) $C(=O)C_{1-7}$alkyl optionally substituted by $NR^7R^8$, aryl, het, $CO_2H$, or $O(CH_2)_nCO_2R^{14}$;

$R^{14}$ is
- (a) H, or
- (b) $C_{1-7}$alkyl;

each n is independently 1, 2, 3, 4 or 5;

each m is independently 0, 1, or 2;

M is sodium, potassium, or lithium;

aryl is a phenyl radical or an ortho-fused bicyclic carbocyclic radical wherein at least one ring is aromatic;

wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;

wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$alkyl which may be further substituted by one to three $SR^{14}$, $NR^{14}R^{14}$, $OR^{14}$, or $CO_2R^{14}$ groups.

2. The compound of claim 1 wherein $R^1$ is Cl.

3. The compound of claim 1 wherein: $R^3$ is selected from the group consisting of $CH_2$-morpholine, alkynyl-$CH_2OH$, $CH_2$-(tetrahydro-2H-pyran-4-yl) and $(CH_2)_3OH$.

4. The compound of claim 1 which is selected from the group consisting of
N-(4-chlorobenzyl)-4-hydroxy-7-methyl[1,8]naphthyridine-3-carboxamide;
N-(4-chlorobenzyl)-4-hydroxy-7-methyl-6-(tetrahydro-2H-pyran-4-ylmethyl)[1,8]naphthyridine-3-carboxamide;
N-(4-chlorobenzyl)-4-hydroxy-7-methyl-6-(4-morpholinylmethyl)[1,8]naphthyridine-3-carboxamide;
6-bromo-N-(4-chlorobenzyl)-4-hydroxy-7-methyl[1,8]naphthyridine-3-carboxamide;
N-(4-chlorobenzyl)-4-hydroxy-6-(3-hydroxy-1-propynyl)-7-methyl[1,8]naphthyridine-3-carboxamide;
N-(4-chlorobenzyl)-4-hydroxy-6-iodo-7-methyl[1,8]naphthyridine-3-carboxamide; and
Methyl 6-{[(4-chlorobenzyl)amino]carbonyl}-5-hydroxy-2-methyl[1,8]naphthyridine-3-carboxylate.

5. A composition of matter comprising a pharmaceutically effective amount of a compound of formula (IV):

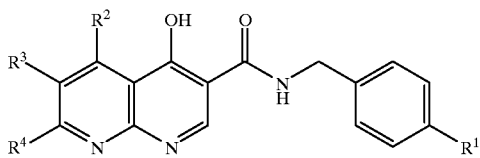

IV or a pharmaceutically acceptable salt thereof wherein, $R^1$ is
- (a) Cl,
- (b) Br,
- (c) CN,
- (d) $NO_2$, or
- (e) F;

$R^2$, $R^3$ and $R^4$ are independently selected from:
- (a) H,
- (b) halo,
- (c) aryl,
- (d) $S(O)_mR^6$,
- (e) $(C=O)R^6$,
- (f) $(C=O)OR^9$,
- (g) cyano,
- (h) het, wherein said het is bound via a carbon atom,
- (i) $OR^{10}$,
- (j) Ohet,
- (k) $NR^7R^8$
- (l) $SR^{10}$,
- (m) Shet,
- (n) $NHCOR^{12}$,
- (o) $NHSO_2R^{12}$, or
- (p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$;

$R^6$ is
- (a) $C_{1-7}$alkyl,
- (b) $NR^7R^8$,
- (c) aryl, or
- (d) het, wherein said het is bound via a carbon atom;

$R^7$ and $R^8$ are independently
- (a) H,
- (b) aryl,
- (c) $C_{1-7}$alkyl which may be partially unsaturated and is optionally substituted by one or more substituents selected from $NR^{10}R^{10}$, $R^{11}$, $SO_mR^9$, $CONR^{10}R^{10}$, or halo, or,
- (d) $R^7$ and $R^8$ together with the nitrogen to which they are attached form a het;

$R^9$ is
- (a) aryl,
- (b) het,
- (c) $C_{3-8}$cycloalkyl,
- (d) methyl, or
- (e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
- (a) H,
- (b) methyl, or
- (b) $C_{2-7}$alkyl optionally substituted by OH;

$R^{11}$ is
- (a) $OR^{10}$,
- (b) Ohet,
- (c) Oaryl,
- (d) $CO_2R^{10}$,
- (e) het,
- (f) aryl, or
- (g) CN;

$R^{12}$ is
- (a) H,
- (b) het,
- (c) aryl, (d) $C_{3-8}$cycloalkyl,
(e) methyl, or
(f) $C_{2-7}$alkyl optionally substituted by $NR^7R^8$ or $R^{11}$;

$R^{13}$ is
(a) $(P=O)(OR^{14})_2$,
(b) $CO(CH_2)_nCON(CH_3)\text{-}(CH_2)_nSO_3^-M^+$,
(c) an amino acid,
(d) $C(=O)$aryl, or
(e) $C(=O)C_{1-7}$alkyl optionally substituted by $NR^7R^8$, aryl, het, $CO_2H$, or $O(CH_2)_nCO_2R^{14}$;

$R^{14}$ is
(a) H, or
(b) $C_{1-7}$alkyl;

each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;
het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups;
and a pharmaceutically effective carrier.

6. The composition of claim 5 wherein $R^1$ is Cl.

7. The composition of claim 5 wherein $R^3$ is selected from the group consisting of $CH_2$-morpholine, alkynl-$CH_2OH$, $CH_2$-(tetrahydro-2H-pyran-4-yl) and $(CH_2)_3OH$.

8. The composition of claim 5 wherein said compound is selected from the group consisting of
N-(4-chlorobenzyl)-4-hydroxy-7-methyl[1,8]naphthyridine-3-carboxamide;
N-(4-chlorobenzyl)-4-hydroxy-7-methyl-6-(tetrahydro-2H-pyran-4-ylmethyl)[1,8]naphthyridine-3-carboxamide;
N-(4-chlorobenzyl)-4-hydroxy-7-methyl-6-(4-morpholinylmethyl)[1,8]naphthyridine-3-carboxamide;
6-bromo-N-(4-chlorobenzyl)-4-hydroxy-7-methyl[1,8]naphthyridine-3-carboxamide;
N-(4-chlorobenzyl)-4-hydroxy-6-(3-hydroxy-1-propynyl)-7-methyl[1,8]naphthyridine-3-carboxamide;
N-(4-chlorobenzyl)-4-hydroxy-6-iodo-7-methyl[1,8]naphthyridine-3-carboxamide; and
Methyl 6-{[(4-chlorobenzyl)amino]carbonyl}-5-hydroxy-2-methyl[1,8]naphthyridine-3-carboxylate.

9. A method of treating or preventing a viral infection, comprising administering to a mammal in need of such treatment, a compound of claim 1.

10. The method according to claim 9 wherein said viral infection is a herpes virus infection.

11. The method according to claim 9 wherein said mammal is a human.

12. The method according to claim 9 wherein said mammal is a livestock or companion animal.

13. The method according to claim 10 wherein the infection is herpes simplex virus type 1, 2, 6, 7, or 8, varicella zoster virus, human cytomegalovirus, or epstein-Barr virus.

14. The method according to claim 9 wherein the amount administered is from about 0.1 to about 300 mg/kg of body weight.

15. The method according to claim 14 wherein the amount administered is from about 1 to about 30 mg/kg of body weight.

16. The method according to claim 9 wherein the compound is administered parenterally, intravaginally, intranasally, topically, orally, or rectally.

17. A method for inhibiting a viral DNA polymerase, comprising contacting the polymerase with an effective inhibitory amount of a compound of claim 1.

18. The method of claim 20 wherein the polymerase and the compound are contacted in vitro.

19. The method of claim 20 wherein the polymerase and the compound are contacted in vivo.

20. A compound selected from the group consisting of:
N-(4-chlorobenzyl)-4-hydroxy-7-methyl[1,8]naphthyridine-3-carboxamide;
N-(4-chlorobenzyl)-4-hydroxy-7-methyl-6-(tetrahydro-2H-pyran-4-ylmethyl)[1,8]naphthyridine-3-carboxamide;
N-(4-chlorobenzyl)-4-hydroxy-7-methyl-6-(4-morpholinylmethyl)[1,8]naphthyridine-3-carboxamide;
6-bromo-N-(4-chlorobenzyl)-4-hydroxy-7-methyl[1,8]naphthyridine-3-carboxamide;
N-(4-chlorobenzyl)-4-hydroxy-6-(3-hydroxy-1-propynyl)-7-methyl[1,8]naphthyridine-3-carboxamide;
N-(4-chlorobenzyl)-4-hydroxy-6-iodo-7-methyl[1,8]naphthyridine-3-carboxamide; and
Methyl 6-{[(4-chlorobenzyl)amino]carbonyl}-5-hydroxy-2-methyl[1,8]naphthyridine-3-carboxylate.

* * * * *